United States Patent [19]
Carr et al.

[11] Patent Number: 4,853,398

[45] Date of Patent: Aug. 1, 1989

[54] LEUKOTRIENE ANTAGONISTS AND USE THEREAS

[75] Inventors: F. P. Carr, Indianapolis; Robert D. Dillard, Zionsville; Doris E. McCullough, Carmel, all of Ind.

[73] Assignee: Eli Lilly and Company, Indianapolis, Ind.

[21] Appl. No.: 38,254

[22] Filed: Apr. 13, 1987

[51] Int. Cl.$^4$ .................. C07D 257/04; A61K 31/41; A61K 31/19; C07C 59/48

[52] U.S. Cl. ................................... 514/381; 548/251; 548/252; 514/561; 514/562; 514/570; 514/571; 562/426; 562/429; 562/430; 562/434; 562/460; 562/463; 560/9; 560/11; 560/12; 560/18; 560/45; 560/46; 560/52; 560/53; 560/57; 560/65; 560/67; 560/70

[58] Field of Search ................ 548/251, 252; 514/381, 514/561, 562, 570, 571; 562/426, 429, 430, 434, 460, 463

[56] References Cited

U.S. PATENT DOCUMENTS

| | | | |
|---|---|---|---|
| 3,899,513 | 8/1975 | Warren et al. | 260/345.2 |
| 4,281,008 | 7/1981 | Chamberlain et al. | 424/269 |
| 4,424,231 | 1/1984 | Bantick et al. | 424/274 |
| 4,474,788 | 10/1984 | Bantick | 424/258 |
| 4,499,299 | 2/1985 | Bernstein et al. | 514/570 |
| 4,567,279 | 1/1986 | Chan | 548/491 |
| 4,617,407 | 10/1986 | Young et al. | 549/462 |
| 4,628,115 | 12/1986 | Carson et al. | 562/464 |
| 4,644,071 | 2/1987 | Masatern et al. | 549/417 |
| 4,650,812 | 3/1987 | Cohen et al. | 514/456 |

FOREIGN PATENT DOCUMENTS

| | | |
|---|---|---|
| 28063 | 5/1981 | European Pat. Off. . |
| 56172 | 7/1982 | European Pat. Off. . |
| 108592 | 5/1984 | European Pat. Off. . |
| 132366 | 1/1985 | European Pat. Off. . |

*Primary Examiner*—David B. Springer
*Attorney, Agent, or Firm*—Robert A. Conrad; Leroy Whitaker

[57] ABSTRACT

This invention provides benzene derivatives which are leukotriene antagonists, formulations of those derivatives, and a method of using those derivatives for the treatment of conditions characterized by an excessive release of leukotrienes.

20 Claims, No Drawings

LEUKOTRIENE ANTAGONISTS AND USE THEREAS

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide novel chemical agents which are selective leukotriene antagonists that can be used therapeutically in the treatment of allergic disorders such as asthma, where leukotrienes are thought to be causal mediators.

SUMMARY OF THE INVENTION

This invention provides for compounds of the Formula I $$\underset{\text{HO}}{\overset{\text{O}}{\underset{\|}{R_1-C}}}\!\!\!\underset{R_2}{\overset{R_3}{\bigcirc}}\!\!\!\underset{R_6}{\overset{R_5}{\underset{|}{C}}}\!\!-Z-\!\!\underset{R_8}{\overset{R_7}{\bigcirc}}\!\!-A-\!\!\underset{R_8}{\overset{R_7}{\bigcirc}}\!\!-Q-R_4 \qquad \text{I}$$

and pharmaceutically acceptable salts thereof, wherein:
$R_1$ is hydrogen, $C_1$–$C_6$ alkyl, $C_3$–$C_8$ cycloalkyl, phenyl-substituted-($C_1$–$C_3$ alkyl), phenyl, or phenyl substituted with a halo, $C_1$–$C_4$ alkyl, or $C_1$–$C_4$ alkoxy functionality;
$R_2$ is $C_1$–$C_{10}$ alkyl, $C_2$–$C_6$ alkenyl, benzyl, or 2-phenylethyl;
$R_3$ is hydrogen, bromo, or chloro;

$$\text{Z is } -\text{O}-, -\text{NR}-, \text{ or } -\overset{(\text{O})_p}{\underset{\|}{\text{S}}}-;$$

$$\text{A is a bond, } -\text{O}-, -\overset{(\text{O})_p}{\underset{\|}{\text{S}}}-, -\text{NR}-, -\overset{\text{O}}{\underset{\|}{\text{C}}}-, -\text{CHOR}- \text{ or}$$

straight or branched chain $C_1$–$C_4$ alkylidene;
Q is a bond or straight or branched chain $C_1$–$C_4$ alkylidene;
$R_4$ is $COR_9$, 5-tetrazolyl, or 3-(1,2,5-thiadiazolyl); where
each R is independently hydrogen, $C_1$–$C_3$ alkyl, or $C_1$–$C_4$ alkanoyl;
each $R_5$ and $R_6$ is independently hydrogen, $C_1$–$C_3$ alkyl, phenyl, or benzyl;
each $R_7$ and $R_8$ is independently hydrogen, $C_1$–$C_4$ alkoxy, halo, hydroxy, amino, nitro, or $C_1$–$C_4$ alkyl; and
$R_9$ is hydroxy or $C_1$–$C_4$ alkoxy.

Further provided by this invention is a method for treating immediate hypersensitivity conditions such as asthma, using compounds of Formula I above and pharmaceutical formulations for these compounds.

DETAILED DESCRIPTION AND PREFERRED EMBODIMENT

The present invention relates to new organic compounds that are useful in the treatment of immediate hypersensitivity reactions. A preferred group of compounds are the compounds of Formula I wherein:
(a) $R_1$ is $C_1$–$C_6$ alkyl, especially methyl,
(b) $R_2$ is $C_1$–$C_6$ alkyl, especially propyl,
(c) $R_3$ is hydrogen,
(d) $R_5$ is hydrogen,
(e) $R_6$ is hydrogen,
(f) Z is $$-\overset{(\text{O})_p}{\underset{\|}{\text{S}}}-,$$

—NH—, or especially —O—,
(g) A is —O—, —CO—, or —CHOH—, and
(h) $R_4$ is —COOH or 5-tetrazolyl.

An especially preferred group of compounds are those of Formula Ia:

$$\underset{}{\overset{\text{O}}{\underset{\|}{CH_3-C}}}\!\!-\!\!\underset{}{\overset{\text{HO } R_2'}{\bigcirc}}\!\!-CH_2-O-\bigcirc-A'-\bigcirc\!\!\underset{\text{HN}\diagdown}{\overset{\diagup \text{N}}{\diagdown}}\!\!\underset{\text{N}}{\overset{}{\diagup}}\quad\text{Ia}$$

and pharmaceutically acceptable salts thereof wherein:
$R_2'$ is $C_1$–$C_6$ alkyl, especially propyl; and
A' is —O—, —CO—, or —CHOH—.

The following definitions refer to the various terms used throughout this disclosure.

The term "$C_1$–$C_{10}$ alkyl" refers to the straight and branched aliphatic radicals of 1 to 10 carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), nonyl, 1-, 2-, 3-, 4-, 5-, 6-, or 7-methyloctyl, 1-, 2-, 3-, 4-, or 5-ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, and the like. The term "$C_1$–$C_{10}$ alkyl" includes within its definition the terms "$C_1$–$C_3$ alkyl", "$C_1$–$C_4$ alkyl", and "$C_1$–$C_6$ alkyl".

The term "$C_3$–$C_8$ cycloalkyl" refers to the saturated alicyclic rings of three to eight carbon atoms such as cyclopropyl, methylcyclopropyl, cyclobutyl, cyclopentyl, cyclohexyl, cyclooctyl, and the like.

The term "$C_2$–$C_6$ alkenyl" refers to straight and branched radicals of two to six carbon atoms such as ethenyl, allyl, isopropenyl, butenyl, isobutenyl, 3-methyl-2-butenyl, n-hexenyl, and the like.

The term "halo" refers to fluoro, chloro, bromo, and iodo. The term "$C_1$-$C_4$ alkoxy" refers to straight and branched alkoxy radicals of up to four carbon atoms, such as methoxy, ethoxy, n-propoxy, isopropoxy, n-butoxy, tert-butoxy, and the like.

The term "$C_1$-$C_4$ alkylidene" refers to straight and branched chain divalent alkyl radicals of one to four carbon atoms such as —$CH_2$—, —$CH_2CH_2$—, —$CH(CH_3)$—, —$C(CH_3)_2$—, —$CH(CH_3)CH_2$—, —$CH(CH_3)CH(CH_3)$—, —$CH_2CH_2CH_2$—, —$CH(CH_3)CH_2CH_2$—, —$CH_2CH(CH_3)CH_2$—, and the like.

The term "$C_1$-$C_4$ alkanoyl" refers to formyl, acetyl, propionyl, butanoyl, and isobutanoyl.

The pharmaceutically acceptable base addition salts of this invention include salts derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine, and the like. The potassium and sodium salt forms are particularly preferred.

It is recognized that if $R_5$ is different from $R_6$, alkyl or alkylidene functionalities are branched, etc., various stereoisomers will exist. This invention is not limited to any particular stereoisomer but includes all possible individual isomers and racemates of the compounds of Formula I.

Some of the compounds of this invention may be prepared by the reaction of a compound of the Formula II

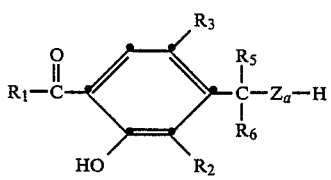

wherein $Z_a$ is —O—, —NR—, or —S—, with a compound of the formula III

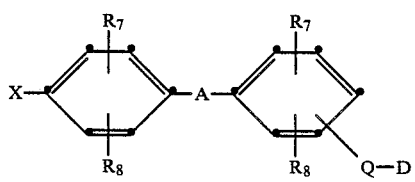

wherein X is a suitable leaving group, such as halo, preferably chloro, and D is —$R_4$, a precursor of —$R_4$, halo, cyano, or a protected acid ester such as a benzhydryl ester. This procedure is useful in preparing the compounds of this invention designated by Formula I'

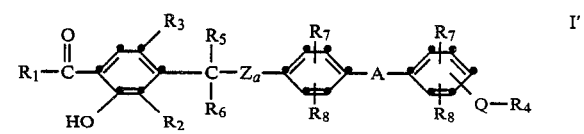

either directly (when D is —$R_4$) or indirectly from intermediates IV

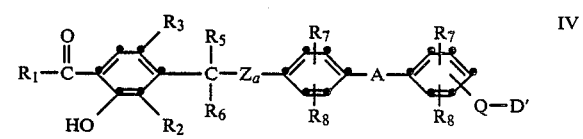

wherein D' is a precursor to —$R_4$, halo, cyano, or a protected acid ester.

The reaction between compounds II and III is usually performed employing equimolar amounts although ratios other than equimolar amounts are completely operative. The reaction is best carried out in a nonreactive solvent such as ketones, especially acetone or methyl ethyl ketone, or dimethylformamide, and in the presence of a base, preferably an alkali metal hydroxide or carbonate, preferably potassium carbonate. Especially when X is chloro, a catalyst such as potassium or sodium iodide may be added to increase the reaction rate. The reaction may be carried out at temperatures of about ambient temperature up to the boiling point of the reaction mixture, the latter being preferred.

In the case where D(D') is cyano, the resulting intermediate IV may be converted to the compounds of this invention by the following methods. Compounds of Formula I' wherein $R_4$ is —COOH may be obtained by hydrolysis of the intermediate cyano derivative. This is generally accomplished by heating the cyano derivative in aqueous alcohol in the presence of a base such as sodium hydroxide. Alternatively, the carboxylic acid derivatives (I', $R_4$ is —COOH) may be prepared by the hydrolysis of the corresponding ester derivatives. This may be accomplished by an aqueous hydrolysis as described above or, especially in the case of a diphenylmethyl (benzhydryl) ester, using methods known in the art such as treating with formic acid and triethylsilane followed by an aqueous workup, acidic hydrolysis, treatment with trifluoroacetic acid in anisole, or catalytic hydrogenation. The required benzhydryl ester starting materials (III, D is a benzhydryl ester) may be prepared from the corresponding carboxylic acids (III, D is —COOH) in the usual ways, such as treatment with diphenyldiazomethane in methylene chloride or heating with benzhydrol and a mineral acid in a solvent such as toluene with the azeotropic removal of water. The compounds of Formula I' wherein $R_4$ is —COO($C_1$-$C_4$ alkyl) may be prepared by conventional methods of esterification from the respective acid derivatives or are prepared directly by the methods described below. Salts may be prepared by treating the corresponding acids ($R_4$ is —COOH) with an appropriate base in the normal manner.

The compounds of Formula I' wherein $R_4$ is 5-tetrazolyl are prepared by treating the cyano intermediate with an alkali metal azide such as sodium azide, ammonium chloride, and (optionally) lithium chloride in a non-reactive high-boiling solvent such as N,N-dimethylformamide, preferably at temperatures from 60° C.

to the reflux temperature of the reaction mixture. Alternatively, tri-n-butyltin azide or tetramethylguanidinium azide may be used in place of the alkali metal azide, ammonium chloride, and lithium chloride. It is preferred that the tetrazole functionality be introduced from the corresponding cyano group as one of the last, if not the last, step of the chemical sequence.

When employing intermediate III wherein D is halo, those skilled in the art will recognize that dihalo intermediate III is non-symmetrically substituted and that X should be a better leaving group than D in order for the desired product IV to be formed. If D is the better leaving group in compound III, III can first be converted to a different intermediate III (e.g., reaction of III (D is halo) with an alkali metal cyanide to give III (where D is —CN)) which can then be reacted with compound II as previously described.

The compounds of Formula IV wherein D' is halo may be transformed into the compounds of this invention in the following manner. When compounds of Formula IV (D' is halo) are heated with an alkali metal cyanide, such as sodium cyanide, in the presence of a high boiling, nonreactive solvent, such as N,N-dimethylformamide, at elevated temperatures (50° C. to the reflux temperature of the solvent), the intermediate cyano compound of Formula IV (D' is cyano) is produced which may be then be transformed into the acid, ester, or tetrazole derivatives as described previously.

Alternatively, I' may be prepared by reacting the appropriate benzyl derivative V

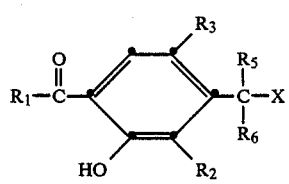

with a derivative of Formula VI

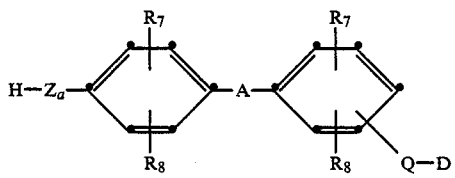

to give compounds I' directly or indirectly through intermediate IV.

Other compounds of Formula I are prepared in a similar manner as taught for the compounds of Formula I'. The compounds of Formula I are prepared directly or indirectly by treating a bromo-compound of the Formula VII

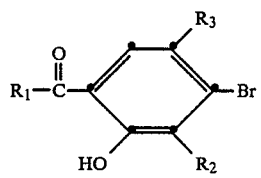

with a strong base, such as lithium diisopropylamide, in an inert solvent, such as diethyl ether, at low temperatures, preferably $-20°$ to $0°$ C., to prepare the lithium salt of VII which is then reacted with III'

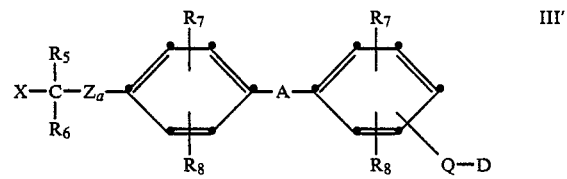

to provide compounds I directly (when D is $-R_4$) or intermediates VIII.

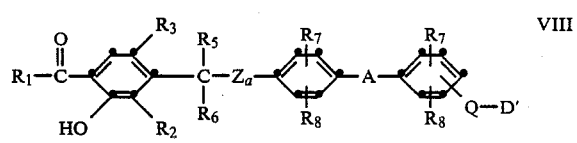

Compounds VIII can then be transformed into I by the same methods of transformation as previously described for converting compounds IV into I'.

The benzhydrol derivatives (A=—CHOH) are readily prepared by reduction of the corresponding benzophenones (A=C=O) by reduction with sodium borohydride. The benzhydrol derivative can be alkylated or acylated by conventional means to form the alkoxy and acyloxy derivatives (A=CHOR). The various amine functionalities (Z or A=NH) may similarly be alkylated or acylated to provide the corresponding alkyl and acyl derivatives. As will be apparent to those skilled in the art, the order of such transformations, upon final products or intermediates thereto, may depend upon the presence of other functional groups.

The 3-(1,2,5-thiadiazoles) of this invention can be prepared by reacting intermediates corresponding to III, I', VI, VIII, and the like where $R_4$ or D is $-CH(NH_2)CONH_2$ with N-methyl-N-(trimethylsilyl)-trifluoroacetamide and thionyl chloride. Once again, the preparation and transformation of such amino acid related intermediates are known to skilled artisans.

The thio derivatives and intermediates of this invention (p is 0) may be transformed into the corresponding sulfoxide (p is 1) compounds upon treatment with a mild oxidizing agent, such as hydrogen peroxide in methanol or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methanol.

In addition, various compounds of Formula I can be prepared from other compounds, precursors, or intermediates of Formula I by standard methods such as hydrolysis, esterification, alkylation, oxidation, reduction, aminolysis, halogenation, and the like, as are well known to those skilled in the art. In the prior discussion, the terms "precursors" and "precursor to $-R_4$" mean those compounds, either related to the final compounds I or any intermediates or starting materials, which can be transformed into the desired functionality $-R_4$. These include the cyano intermediates and intermediates which may be transformed into the title products by any of the above mentioned methods known to those skilled in the art.

Intermediates II and V are disclosed in European Patent Application Publication No. 132,366 which is expressly incorporated into this application by reference. All other intermediate compounds and necessary reagents are either commercially available, known in the literature, or can be prepared according to methods known in the art.

As is well known in the art, the $R_3$ chloro and bromo derivatives may be prepared by halogenation of the corresponding hydrogen compounds ($R_3$ is hydrogen) of this invention (I) or of the intermediates XV.

The following preparations and examples further illustrate the preparation of the starting materials, intermediates, and compounds of the invention. The examples are illustrative only and are not intended to limit the scope of the invention. Where structures were confirmed by infra-red or proton nuclear magnetic resonance analysis, the compound is so designated by "IR" and/or "NMR", respectively.

EXAMPLE 1

1-[2-Hydroxy-3-propyl-4-({4-[3-(1H-tetrazol-5-yl)benzoyl]phenoxy}methyl)phenyl]ethanone

A. Preparation of 3-cyanobenzoyl chloride

A mixture of 50 g. of 3-cyanobenzoic acid and 100 ml. of thionyl chloride were stirred overnight in 500 ml. of methylene chloride. The solvent and excess thionyl chloride were removed in vacuo providing 55.3 g. of crude subtitle intermediate which was used without further purification.

Analysis for $C_8H_4ClNO$: Calculated: C, 58.03; H, 2.44; N, 8.46; Found: C, 58.24; H, 2.61; N, 8.26.

B. Preparation of 4-(3-cyanobenzoyl)anisole

Under a nitrogen atmosphere, 16.5 g. of 3-cyanobenzoyl chloride were added to 80 ml. of methylene chloride. The temperature was brought to approximately 0° C. by means of an external ice bath and kept cold while 20 g. of aluminum chloride were added in portions. A solution of 10.8 g. of anisole in 20 ml. of methylene chloride were added to the reaction solution. The mixture was allowed to warm to room temperature and stirred overnight. The mixture was poured into a mixture of ice water/hydrochloric acid and extracted with ethyl acetate. The layers were separated and the organic layer was washed with water, dried, and concentrated in vacuo. The residue was crystallized from toluene/hexane to which a small amount ethyl acetate had been added to provide 7.7 g. of the desired subtitle intermediate, m.p. 85°–88° C.

Analysis for $C_{15}H_{11}NO_2$: Calculated: C, 75.94; H, 4.67; N, 5.90; Found: C, 75.88; H, 4.83; N, 5.99.

C. Preparation of 4-(3-cyanobenzoyl)phenol.

To a solution of 7 g. of 4-(3-cyanobenzoyl)anisole and 75 ml. of methylene chloride were added 11.8 g. of aluminum chloride. The reaction was stirred overnight at room temperature and then heated at reflux for 24 hours. The cooled reaction mixture was poured into ice water/hydrochloric acid and extracted with ethyl acetate. The layers were separated and the organic layer was washed with water, dried, and concentrated in vacuo. The residue was crystallized from toluene/hexane to which a small amount ethyl acetate had been added to provide 5.3 g. of the desired subtitle intermediate, m.p. 153°–157° C.

Analysis for $C_{14}H_9NO_2$: Calculated: C, 75.33; H, 4.06; N, 6.27; Found: C, 75.10; H, 4.07; N, 6.22.

D. Preparation of 1-(2-hydroxy-3-propyl-4-{[4-(3-cyanobenzoyl)phenoxy]methyl}phenyl)ethanone Under a nitrogen atmosphere, 1.96 g. of potassium t-butoxide was stirred at room temperature in 50 ml. of ethanol. Five grams of the intermediate from Example 1C were added followed by the addition of 3.39 g. of 4-acetyl-3-hydroxy-2-propylbenzyl chloride and 2.25 g. of sodium iodide. The reaction was stirred at room temperature for 4 days. Two hundred milliliters of water were added, the solution was acidified with hydrochloric acid, and, after 2 hours, the resulting precipitate was recovered by filtration. The solid was dissolved with ethyl acetate, dried, and concentrated in vacuo. The residue was dissolved in toluene containing a small amount ethyl acetate and hexane was added. The resulting precipitate was recovered by filtration and purified by high pressure liquid chromatography over silica gel eluting with 9:1 toluene/ethyl acetate providing 3.6 g. of the desired subtitle intermediate, m.p. 146°–148° C.

Analysis for $C_{20}H_{23}NO_4$: Calculated: C, 75.72; H, 5.61; N, 3.38; Found: C, 76.34; H, 5.79; N, 3.46.

E. Preparation of 1-[2-hydroxy-3-propyl-4-({4-[3-(1H-tetrazol-5-yl)benzoyl]phenoxy}methyl)phenyl]-ethanone A mixture of 3.5 g. of the nitrile of Example 1D and 13.28 g. of tri-n-butyltin azide were heated at reflux in glyme for 3 days. The cooled reaction mixture was poured into acidified ice water and stirred for 1 hour. The mixture was extracted with ethyl acetate and the organic layer was washed with water, dried, and concentrated in vacuo. Purification by high pressure liquid chromatography over silica gel eluting with 9:1 methylene chloride/methanol to which 0.5% acetic acid had been added to provide 2.5 g. of the title product, m.p. 208°–214° C. Recrystallization from ethyl acetate/hexane provided material having the following analysis.

Analysis for $C_{26}H_{24}N_4O_4$: Calculated: C, 68.41; H, 5.30; N, 12.27; Found: C, 68.18; H, 5.48; N, 12.13.

EXAMPLES 2–5

The following compounds were prepared from the corresponding nitrile according to the procedure of Example 1E.

2. 1-[2-Hydroxy-3-propyl-4-({4-[4-(1H-tetrazol-5-yl)benzoyl]phenoxy}methyl)phenyl]ethanone, 54% yield, m.p. 185°–188° C.

Analysis for $C_{26}H_{24}N_4O_4$: Calculated: C, 68.41; H, 5.30; N, 12.27; Found: C, 66.38; H, 5.56; N, 11.70.

3. 1-{2-Hydroxy-4-[(4-{hydroxy[3-(1H-tetrazol-5-yl)phenyl]methyl}phenoxy)methyl]-3-propylphenyl}ethanone, 75% yield, m.p. 152°–155° C.

Analysis for $C_{26}H_{26}N_4O_4$: Calculated: C, 68.11; H, 5.72; N, 12.22; Found: C, 68.24; H, 6.00; N, 11.92.

4. 1-[2-Hydroxy-3-propyl-4-({4-[4-(1H-tetrazol-5-yl)phenoxy]phenoxy}methyl)phenyl]ethanone, 81% yield, m.p.=177°–180° C.

Analysis for $C_{25}H_{24}N_4O_4$: Calculated: C, 67.55; H, 5.44; N, 12.60; Found: C, 67.67; H, 5.72; N, 12.38.

5. 1-[2-Hydroxy-3-propyl-4-({4-[3-(1H-tetrazol-5-yl)phenoxy]phenoxy}methyl)phenyl]ethanone, 19% yield, m.p.=60°–70° C. (glass).

Analysis for $C_{25}H_{24}N_4O_4$: Calculated: C, 67.55; H, 5.44; N, 12.60; Found: C, 66.35; H, 5.72; N, 11.94.

The compounds of Formula I should be useful in treating any condition, including clinical conditions, which is characterized by excessive release of leukotrienes $C_4$, $D_4$, or $E_4$. These conditions include immediate type hypersensitivity reactions such as asthma. Evidence obtained over the past few years has shown the presence of leukotrienes in sputum of patients with chronic bronchitis (Turnbull, et al., *Lancet II*, 526 (1977)) and cystic fibrosis (Cromwell, et al., *Lancet II*, 164 (1981)), suggesting a role of leukotrienes in the pathology of those diseases. Furthermore, Lewis and colleagues [*Int. J. Immunopharmacology*, 4, 85 (1982)] have recently detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes.

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, and the species of the mammal involved. As will be appreciated by those skilled in the art, the success of treating a mammal suffering from or susceptible to a condition characterized by an excessive release of leukotrienes with a compound of formula I will be measured by the regression or prevention of the symptoms of the condition.

Leukotriene antagonism was demonstrated by the following test procedure:

Male, Hartley guinea pigs weighing 200–450 grams were killed by decapitation. A section of terminal ileum was removed, the lumen cleaned, and the tissue divided into 2.5 cm. segments. The ilea were mounted in 10 ml. tissue baths containing Krebs-bicarbonate solution of the following composition in mmoles/liter: KCl, 4.6; $CaCl_2.2H_2O$, 1.2; $KH_2PO_4$, 1.2; $MgSO_4.7H_2O$, 1.2; NaCl, 118.2; $NaHCO_3$, 24.8; and dextrose, 10.0. The bath fluid was maintained at 37° C. and aerated with 95 percent oxygen and 5 percent $CO_2$. In addition, the buffer contained $1 \times 10^{-6}M$ atropine to reduce ileal spontaneous activity. Isometric measurements were made with a Grass FTO3C force-displacement transducer and recorded on a Grass polygraph as change in grams of force. A passive force of 0.5 g. was applied to the tissues. After an appropriate equilibration period, single submaximal control responses to pure $LTD_4$ were obtained. Following a five minute exposure of the ileum to an experimental drug, the control concentration of $LTD_4$ was added to the tissue bath. The response of the ileum to $LTD_4$ in the presence of the drug was compared to the response in the absence of the drug. Various degrees of $LTD_4$ antagonism were obtained using 2–4 different concentrations of an experimental compound on a single ileum. The antagonist concentration that produced 50% inhibition of the $LTD_4$ responses ($-\log IC_{50}$) was interpolated from these data using linear regression.

The testing of the compounds of Formula I in these two procedures is summarized in Table I.

TABLE I

| Compound of Example No. | Percent inhibition of $LTD_4$ evoked ileal contractions | | | | | | |
|---|---|---|---|---|---|---|---|
| | Compound Concentration | | | | | | |
| | $3 \times 10^{-7}$ M | $1 \times 10^{-7}$ M | $3 \times 10^{-8}$ M | $1 \times 10^{-8}$ M | $3 \times 10^{-9}$ M | $1 \times 10^{-9}$ M | $-\log IC_{50}$ |
| 1 | 98% | | 80% | | 53% | 21% | 8.58 |
| 2 | | | | 72% | 32% | | 8.29 |
| 3 | | 81% | 75% | 40% | | | 7.89 |
| 4 | 80% | 53% | 25% | | | | 7.08 |

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to 500 mg. (from about 5 to 50 mg. in the case of parenteral or inhalation administration, and from about 25 to 500 mg. in the case of oral or rectal administration) of a compound of Formula I. Dosages of from about 0.5 to 300 mg./kg. per day, preferably 0.5 to 20 mg./kg., of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl, lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

The following formulation examples may employ as active compounds any of the compounds of this invention. The examples are illustrative only and are not intended to limit the scope of the invention in any way.

EXAMPLE 6

Hard gelatin capsules are prepared using the following ingredients:

|  | Quantity (mg/capsule) |
|---|---|
| 1-[2-hydroxy-3-propyl-4-({4-[3-(1H—tetrazol-5-yl)benzoyl]-phenoxy}methyl)phenyl]ethanone hydrochloride | 250 |
| Starch | 200 |
| Magnesium stearate | 10 |

The above ingredients are mixed and filled into hard gelatin capsules in 460 mg. quantities.

EXAMPLE 7

A tablet is prepared using the ingredients below:

|  | Quantity (mg/tablet) |
|---|---|
| 1-{2-hydroxy-4-[(4-{hydroxy[3-(1H—tetrazol-5-yl)phenyl]-methyl}phenoxy)methyl]-3-propylphenyl}ethanone sulfate | 250 |
| Cellulose, microcrystalline | 400 |
| Silicon dioxide, fumed | 10 |
| Magneium stearate | 5 |

The components are blended and compressed to form tablets each weighing 665 mg.

EXAMPLE 8

An aerosol solution is prepared containing the following components:

|  | Weight % |
|---|---|
| 1-[2-hydroxy-3-allyl-4-({4-[4-(1H—tetrazol-5-yl)-1,6-dichlorobenzoyl]-phenoxy}methyl)phenyl]hexanone | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

EXAMPLE 9

Tablets each containing 60 mg. of active ingredient are made up as follows:

| | |
|---|---|
| 1-[2-hydroxy-3-propyl-4-({4-[4-(1H—tetrazol-5-yl)phenoxy]phenoxy}-methyl)phenyl]ethanone | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 10

Capsules each containing 80 mg. of medicament are made as follows:

| | |
|---|---|
| 2-hydroxy-3-ethyl-4-[{4-[4-(1H—tetrazol-5-yl)phenylsulfonyl]-phenylamino}methyl)benzophenone | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 11

Suppositories each containing 225 mg of active ingredient are made as follows:

| | |
|---|---|
| 1-{2-hydroxy-3-methyl-4-[(4-{4-[4-(1H—tetrazol-5-yl)phenyl]butyl}-phenoxy)methyl]phenyl}ethanone | 225 mg. |
| Unsaturated or saturated fatty acid glycerides to | 2,000 mg. |

The active ingredient is passed through a No. 60 mesh U.S. sieve and suspended in the fatty acid glycerides previously melted using the minimum heat necessary. The mixture is then poured into a suppository mold of nominal 2 g. capacity and allowed to cool.

EXAMPLE 12

Suspensions each containing 50 mg. of medicament per 5 ml. dose are made as follows:

| | |
|---|---|
| 1-[2-hydroxy-3-isopropyl-5-chloro-4-({4-[2-(1H—tetrazol-5-yl)benzoyl]-phenylsulfinyl}methyl)phenyl]ethanone | 50 mg. |
| Sodium carboxymethyl cellulose | 50 mg. |
| Sugar | 1 g. |
| Methyl paraben | 0.05 mg. |
| Propyl paraben | 0.03 mg. |
| Flavor | q.v. |
| Color | q.v. |
| Purified water to | 5 ml. |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

We claim:

1. A compound of the Formula

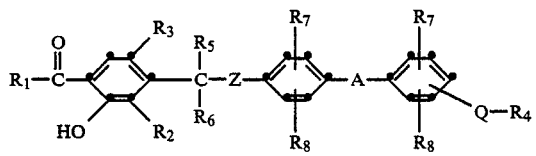

and pharmaceutically acceptable salts thereof, wherein:

$R_1$ is hydrogen, $C_1$–$C_6$ alkyl, $C_3$–$C_8$ cycloalkyl, phenyl-substituted-($C_1$–$C_3$ alkyl), phenyl, or phenyl substituted with a halo, $C_1$–$C_4$ alkyl, or $C_1$–$C_4$ alkoxy functionality;

$R_2$ is $C_1$–$C_{10}$ alkyl, $C_2$–$C_6$ alkenyl, benzyl, or 2-phenylethyl;

$R_3$ is hydrogen, bromo, or chloro;

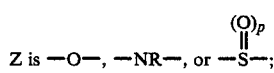

Z is —O—, —NR—, or —S—;

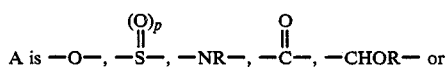

A is —O—, —S—, —NR—, —C—, —CHOR— or straight or branched chain $C_1$–$C_4$ alkylidene;

Q is a bond or straight or branched chain $C_1$–$C_4$ alkylidene;

$R_4$ is $COR_9$, or 5-tetrazolyl; and p is 0, 1, or 2; where each R is independently hydrogen, $C_1$–$C_3$ alkyl or $C_1$–$C_4$ alkanoyl;

each $R_5$ and $R_6$ is independently hydrogen, $C_1$–$C_3$ alkyl, phenyl, or benzyl;

each $R_7$ and $R_8$ is independently hydrogen, $C_1$–$C_4$ alkoxy, halo, hydroxy, amino, nitro, or $C_1$–$C_4$ alkyl; and $R_9$ is hydroxy.

2. A compound of claim 1 wherein $R_1$ is methyl.

3. A compound of claim 2 of the formula

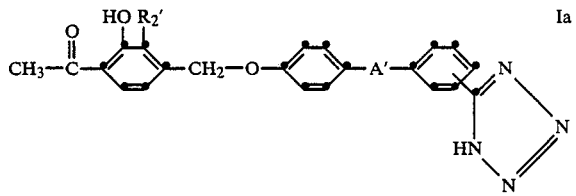

and pharmaceutically acceptable salts thereof wherein:
$R_2'$ is $C_1$–$C_6$ alkyl, especially propyl; and
$A'$ is —O—, —CO—, or —CHOH—.

4. A compound of claim 3 wherein $R_2'$ is propyl.

5. The compound of claim 4 which is 1-[2-hydroxy-3-propyl-4-({4-[3-(1H-tetrazol-5-yl)benzoyl]-phenoxy}methyl)phenyl]ethanone or a pharmaceutically acceptable salt thereof.

6. The compound of claim 4 which is 1-[2-hydroxy-3-propyl-4-({4-[4-(1H-tetrazol-5-yl)benzoyl]-phenoxy}methyl)phenyl]ethanone or a pharmaceutically acceptable salt thereof.

7. The compound of claim 4 which is 1-{2-hydroxy-4-[(4-{hydroxy[3-(1H-tetrazol-5-yl)phenyl]-methyl}phenoxy)methyl]-3-propylphenyl}ethanone or a pharmaceutically acceptable salt thereof.

8. The compound of claim 4 which is 1-[2-hydroxy-3-propyl-4-({4-[4-(1H-tetrazol-5-yl)phenoxy]-phenoxy}methyl)phenyl]ethanone or a pharmaceutically acceptable salt thereof.

9. A method of treating a mammal suffering from or susceptible to any condition characterized by an excessive release of leukotrienes, which comprises administering to said mammal a leukotriene antagonizing amount of a compound of claim 1.

10. A method of treating a mammal suffering from or susceptible to any condition characterized by an excessive release of leukotrienes, which comprises administering to said mammal a leukotriene antagonizing amount of a compound of claim 4.

11. A method according to claim 10 employing 1-[2-hydroxy-3-propyl-4-({4-[3-(1H-tetrazol-5-yl)benzoyl]-phenoxy}methyl)phenyl]ethanone or a pharmaceutically acceptable salt thereof.

12. A method according to claim 10 employing 1-[2-hydroxy-3-propyl-4-({4-[4-(1H-tetrazol-5-yl)-benzoyl]-phenoxy}methyl)phenyl]ethanone or a pharmaceutically acceptable salt thereof.

13. A method according to claim 10 employing 1-{2-hydroxy-4-[(4-{hydroxy[3-(1H-tetrazol-5-yl)-phenyl]-methyl}phenoxy)methyl]-3-propylphenyl}ethanone or a pharmaceutically acceptable salt thereof.

14. A method of treating a mammal suffering from or susceptible to an immediate hypersensitivity reaction of the type represented by asthma, which comprises administering to said mammal a therapeutically-effective amount of a compound of claim 1.

15. A pharmaceutical formulation comprising a compound of claim 1 in association with a pharmaceutically acceptable carrier.

16. A pharmaceutical formulation comprising a compound of claim 4 in association with a pharmaceutically acceptable carrier.

17. A pharmaceutical formulation according to claim 16 employing 1-[2-hydroxy-3-propyl-4-({4-[3-(1H-tetrazol-5-yl)benzoyl]phenoxy}methyl)phenyl]ethanone or a pharmaceutically acceptable salt thereof.

18. A pharmaceutical formulation according to claim 16 employing 1-[2-hydroxy-3-propyl-4-({4-[4-(1H-tetrazol-5-yl)benzoyl]phenoxy}methyl)phenyl]ethanone or a pharmaceutically acceptable salt thereof.

19. A pharmaceutical formulation according to claim 16 employing 1-{2-hydroxy-4-[(4-{hydroxy[3-(1H-tetrazol-5-yl)phenyl]methyl}phenoxy)methyl]-3-propylphenyl}ethanone or a pharmaceutically acceptable salt thereof.

20. A pharmaceutical formulation according to claim 16 employing 1-[2-hydroxy-3-propyl-4-({4-[4-(1H-tetrazol-5-yl)phenoxy]phenoxy}methyl)phenyl]ethanone or a pharmaceutically acceptable salt thereof.

* * * * *